Figure 1:
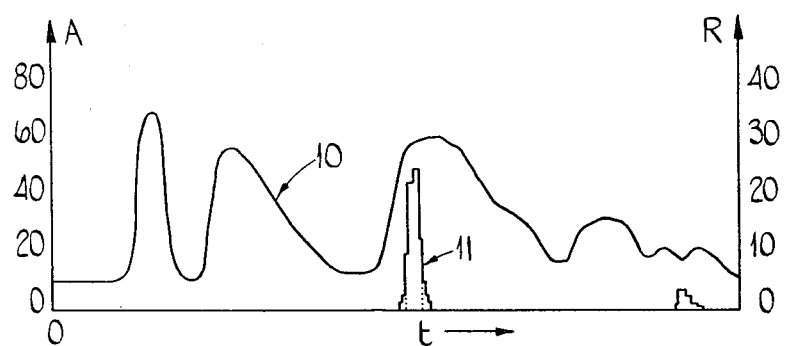

United States Patent [19]

Bradwell et al.

[11] 4,279,884

[45] Jul. 21, 1981

[54] PROCESS FOR PREPARATION OF ANTISERA

[75] Inventors: Arthur R. Bradwell, Harborne; David Burnett, Finchfield, both of England

[73] Assignee: University of Birmingham, Birmingham, England

[21] Appl. No.: 825,126

[22] Filed: Aug. 16, 1977

[30] Foreign Application Priority Data

Aug. 25, 1976 [GB] United Kingdom ............... 35319/76

[51] Int. Cl.³ .................... A61K 33/48; A61K 49/00; A61K 43/00; C07G 7/00
[52] U.S. Cl. .................................... 424/1; 260/112 B; 424/1.5; 424/9; 424/12; 424/85; 424/88
[58] Field of Search ..................... 424/1, 12, 9, 85, 88; 23/230 B; 260/112 B

[56] References Cited

U.S. PATENT DOCUMENTS

| 3,284,434 | 11/1966 | Sutherland | 424/12 |
|---|---|---|---|
| 4,026,879 | 5/1977 | Spector | 424/1 |
| 4,041,076 | 8/1977 | Avenia et al. | 424/1 |

FOREIGN PATENT DOCUMENTS 55663 6/1973 Romania ................................... 424/12

OTHER PUBLICATIONS

Smith et al., Immunology, 7, p. 111 (1964).
Shivers et al., Immunology 13, p. 547 (1967).
Crowle et al., Immunological Communications, 1 (4), 1972, pp. 325-336.
Nansen et al., Acta Patn. Microbiol. Scand., Section B. 79, 1971, pp. 459-465.

Primary Examiner—Benjamin R. Padgett
Assistant Examiner—Christine M Nucker
Attorney, Agent, or Firm—Ladas & Parry

[57] ABSTRACT

A process for the preparation of a high titre antiserum of a desired specificity includes the steps of, a first immunological reaction between a serum sample which includes a protein to which the required antiserum is specific and an antiserum sample known to include the required antiserum, injecting into an animal a first selected antigen/antibody comples from the aforesaid first reaction, withdrawal of serum from the animal, performing a second immunological reaction between the withdrawn serum and a serum sample which includes the protein to which the required antiserum is specific, and selecting a second antigen/antibody comples from the second reaction, the first and second selected complexes including the required antiserum.

7 Claims, 9 Drawing Figures

PROCESS FOR PREPARATION OF ANTISERA

This invention relates to processes for the preparation of antisera which are specific to one or more selected proteins.

It is known to produce an antiserum by injection into an animal of a serum which contains the protein against which the antiserum is required to act. It has, in the past, proved difficult or impossible to isolate particular proteins from serum samples, so that even when highly refined serum samples are injected, the antisera produced as a result have been specific to a relatively large number of proteins.

It is an object of the invention to provide a process for the preparation of high titre antisera which are specific to a relatively small number of proteins.

According to the invention a process for the preparation of an antiserum includes the steps of:
(i) reacting, by means of immunological analysis, a serum sample which includes a protein to which the required antiserum is specific, with a first antiserum sample which is known to include the required specific antiserum,
(ii) selecting, from the results of the aforesaid reaction, of a first antigen/antibody complex which corresponds to the protein to which the required antiserum is specific,
(iii) injecting the antigen/antibody complex into an animal,
(iv) subsequent withdrawal of serum from the animal
(v) using the withdrawn serum as a second antiserum sample for a further immunological analysis in conjunction with a serum sample which includes the protein to which the required antiserum is specific.

The invention also resides in an antiserum when prepared by a method according to the invention.

The invention further resides in determining the quantity of a protein in a serum sample by reacting the serum sample with an antiserum prepared by a method as above defined.

A process according to the invention will now be described by way of example only, and in relation to the production of an antiserum for human serum thyroxine binding globulin (TBG).

Figure 5:
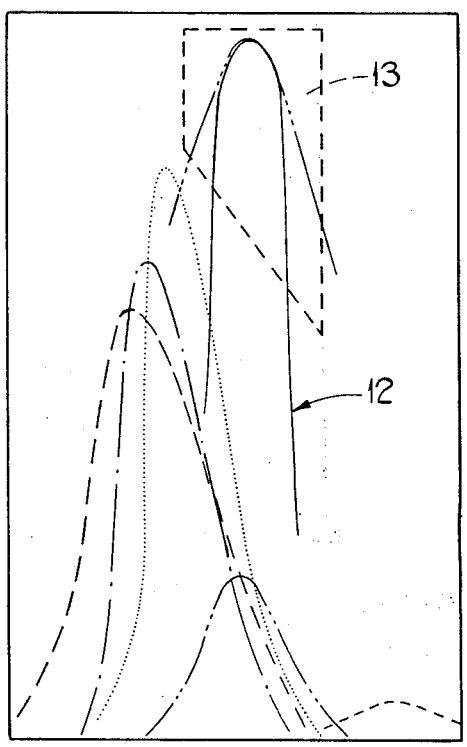
Figure 6:
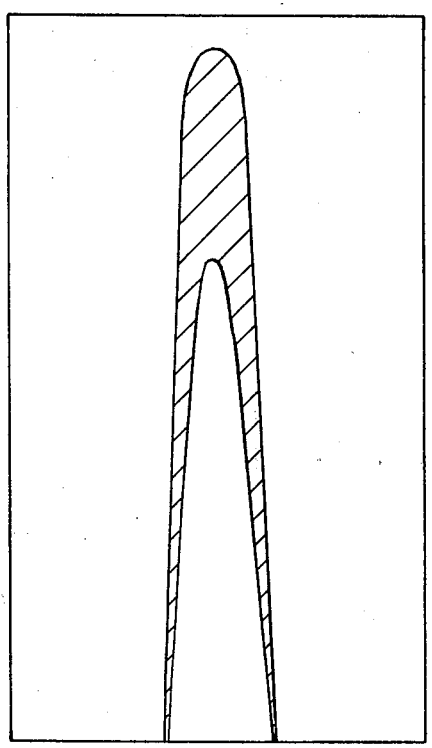
Figure 7:
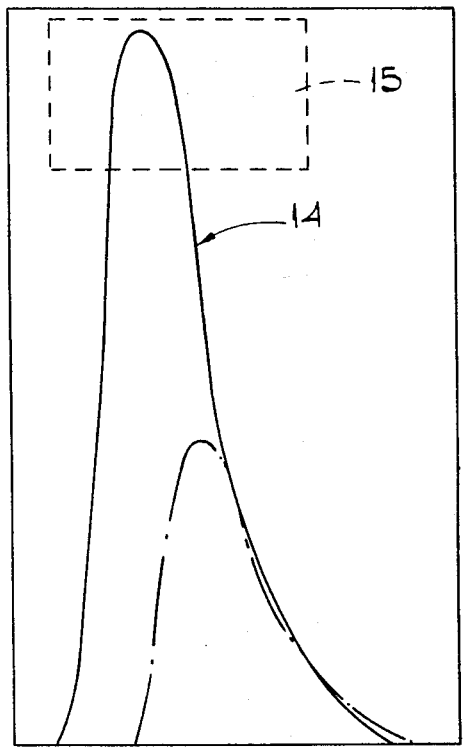
Figure 8:
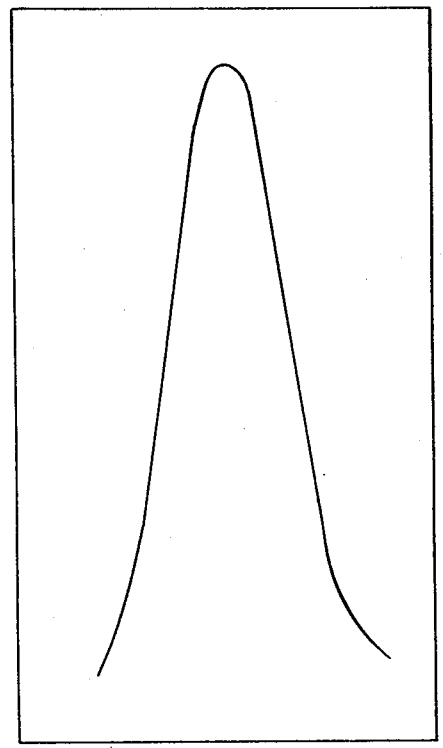
Figure 9:
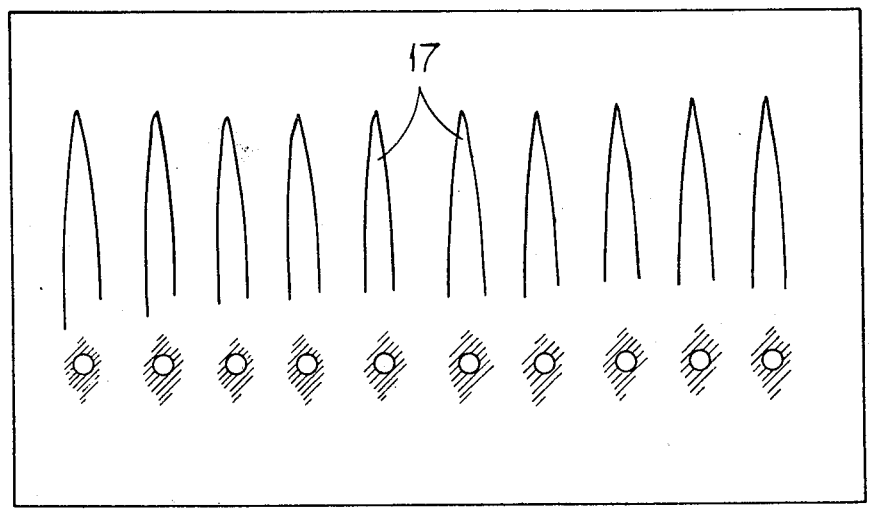

In the accompanying drawings:

FIGS. 1 to 4 show steps in the partial purification of human TBG,

FIGS. 5 and 6 indicate the results of a first two-dimensional immunoelectrophoresis analysis employing the partially—purified TBG and antiserum produced therefrom, FIG. 7 indicates the results of a second two-dimensional immunoelectrophoresis analysis employing human serum and an atiserum which was produced as a result of the first analysis, FIG. 8 indicates the results of a third two-dimensional immunoelectrophoresis analysis employing human serum and an antiserum which was produced as a result of the second analysis, and FIG. 9 shows the result of a comparative immunoelectrophoresis test on an antiserum sample prepared by a method according to the invention.

As a first step a sample of human thyroxine binding globulin was partially purified by physical means. A four-stage procedure was employed, using the fact that iodine binds to T.B.G.

(a) a first Ion-exchange chromatography stage,
(b) a second Ion-exchange chromatography stage,
(c) a gel chromatography stage, and
(d) a Polyacrylamide gel electrophoresis stage.

Stage (a) comprised ion-exchange chromatography of 500 ml of human serum to which $^{125}I$-T4 had been added, and was carried out on a di-ethyl-amino-ethyl-cellulose column ($60 \times 5$ cm) using increasing concentrations of 0.05 M–0.5 M tris/HCl, pH8, as the elution buffer. In this and the subsequent ion-exchange stage the concentration gradient of the elution buffer was controlled by an "Ultragrad" device, obtained from L.K.B. Industries, a Swedish Company. The major radioactive peak emerging from the column was concentrated in an ultra-filtration cell obtained from Amicon Limited. The percentage absorption A, of light at a wavelength of, 254 nanometers, by serum fractions obtained from the cellulose column, is shown in FIG. 1 as a curve 10 plotted against time t. FIG. 1 also shows, at 11, the radiation level R, in counts/minute $\times 10^{-3}$. It will be seen that the fraction, or fractions, containing the T.B.G. could readily be identified. One or more of these fractions provided a concentrate for use in stage (b).

For stage (b) the concentrate was subjected to chromatography under the same conditions as stage (a) but on a smaller column ($40 \times 2.5$ cm). The solution containing the major radioactive peak was again concentrated, with the result indicated in FIG. 2.

Figure 2:
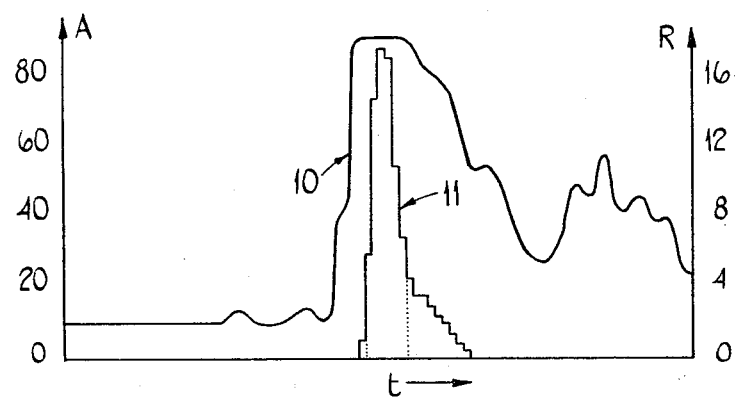
Figure 3:
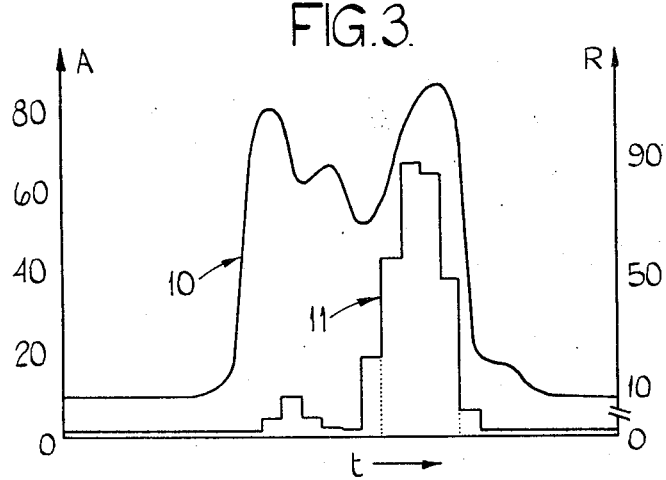

In stage (c) the solution obtained from stage (b) was applied to a column ($90 \times 2.5$ cm) of "Sephadex G-150" a beaded Sepharose compound obtainable from Pharmacia, a Swedish Company, and eluted using 0.04 M Iris/Citric acid, pH 8.6, containing 0.55 M NaCl as buffer. FIG. 3, corresponding to FIGS. 1 and 2, shows that the fractions containing the radioactive T.B.G. could readily be identified, and these fractions were pooled, concentrated and dialysed against distilled water at 4° C. for 16 hours.

Figure 4:
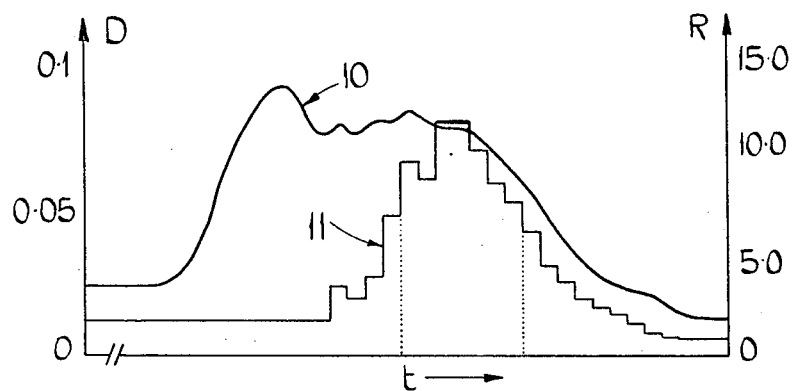

In stage (d) a commercial version of a Gordon and Louis apparatus (as described by A. H. Gordon and L. M. Lewis in "Analytical Biochemistry" 1967 Vol 21 at page 190) was used for polyacrylamide gel electrophoresis of the dialysed solution using a 10% acrylamide gel containing 5% bisacrylamide. The gel buffer, tank and elution buffers were 0.0083 Iris/0.025 glycine, pH 8.4, with an elution rate of 25 ml/hr. The applied potential was 250 volts. The individual fractions were monitored for radioactivity and their optical density D u.v light at 254 nm was determined. Again the fractions containing the major portion of the radioactivity were readily identifiable, as shown in FIG. 4, and were pooled and concentrated.

The partially-purified T.B.G. sample was further purified, for use as an antigen, by subjecting the sample to a first immunological analysis, effected by antibody coupling in an agarose gel. 5 $\mu$l of the partially-purified T.B.G. sample ($\approx 3\%$ of the total protein in the sample) was mixed with 1 $\mu$l of $^{125}I$-T4 (about 1000 counts per minute) and subjected to 2-dimensional immunoelectrophoresis (hereinafter referred to as 2.D.I.E.P.) in 1% agarose gel using Barbitone/sodium Barbitone buffer as previously described by A. R. Bradwell and D. Burnett in Clin. Chim. Acta 58, (1975) pages 283–290.

The second dimension gel contained 200 $\mu$l of an antiserum prepared in a sheep against a $OX_1$ electrophoretic fraction of a serum known to contain T.B.G.. This antiserum contained a high titre antibody to T.B.G.

After electrophoresis for 24 hours at 20 volts the gel was covered with a thin layer of polyethene sheet to prevent drying. A Kodak RP Xomat film was superimposed in the dark for 24 hours and the film processed in a RP Xomat processor model M6 (Kodak Ltd U.K.) FIG. 5 indicates the pattern of precipitates formed in the second-dimension gel, and FIG. 6 indicates the pattern obtained from the exposed film. The $^{125}$I-T4-labelled T.B.G./antibody precipitate could be distinguished from nine other proteins that had formed precipitate arcs in the gel.

The T.B.G. precipitin arc is indicated at 12 in FIG. 5. An area 13 of the agarose gel containing the T.B.G. precipitin arc was sectioned from the rest of the gel. The removed area 13 was homogenised, mixed with 0.25 ml of Freund's complete adjuvant and injected intramuscularly into a sheep. Ten days later a similar gel/T.B.G. precipitate peak was injected into the same sheep. At 20 days the sheep showed circulating antibodies directed against two proteins of fresh human serum, when assessed by a second 2D.I.E.P. immunological analysis (as described above). The T.B.G. peak 14 was again identified by autoradiography as shown in FIG. 7.

A T.B.G. precipitate sample 15 was removed from the gel after completion of the identification process shown in FIG. 7. The sample 15 was used for immunising a second sheep, as described above with reference to the sample 13. After 20 days the sheep plasma contained a monospecific high titre antibody to T.B.G.

The results of an assessment, by 2D.I.E.P. of the plasma withdrawn from the second sheep, are indicated at FIG. 8.

It will be apparent that had the results of the second immunological analysis described with reference to FIG. 7 shown that serum withdrawn from the first sheep was monospecific, that is, had produced the result indicated at FIG. 8, the injection of the second sheep would have been unnecessary.

It will also be apparent that sequences of immunological analysis, sample selection, and injection of the selected sample, may be repeated as often as is necessary to obtain an antiserum of the required specificity, without departing from the principle of the invention.

It will be understood that if a partially-purified serum sample is initially available, the physical purification stages (a) to (d) may be omitted. It will also be understood that stages (a) to (d) may be omitted and the immunological analysis steps repeated as often as necessary to obtain an antiserum which is monospecific or which has a desired specificity.

Furthermore, if an antiserum is initially available, which contains the desired high titre antiserum, there will be no need to prepare this antiserum in a sheep, or other animal, before carrying out the first immunological analysis.

It is an advantage of the invention that for the second, and any subsequent, immunological analysis a fresh serum sample may be used, there being no need for any purification process on these latter serum samples. Risk of damage to the samples is thereby substantially reduced.

A particular use of a high titre monospecific antiserum resides in determining the level, in a serum sample, of the protein to which the antiserum is specific.

Human thyroxine binding globulin (T.B.G.) is an a$_1$ serum protein (Mol. wt.=65,000) that transports 70–75% of the circulating thyroxine (T4) and 3,3',5-triiodothyronine (T3). Most of the remaining T3 and T4 are transported by thyroxine binding prealbumin and albumin so that approximately 0.04% of the T4 is not protein bound but "free" and thereby available for tissue uptake. The concentration of binding proteins varies markedly from patient to patient and T.B.G. in particular may be affected by genetic factors, pregnancy or exogenous oestrogen. Estimates of total serum T3 and T4 may not, therefore, directly reflect the free hormone levels. Biochemical evaluation of thyroid status is therefore dependent not only on the concentration of circulating hormone but on T.B.G. concentration (as the most important transporting protein). Because of the normally low serum concentration of T.B.G. (5–30 mg/L) and difficulties associated with its isolation, most methods of assay have been indirect, estimating binding capacity rather than concentration.

Direct assay of T.B.G. concentration rather than capacity is preferred because it obviates contributions from less specific binding proteins and is not affected by substances, e.g. drugs, that might compete with the hormone for protein binding sites.

FIG. 9 indicates the result of a test using the prepared monospecific T.B.G. antiserum to measure the level of T.B.G. in a serum sample, under optimal conditions. This test used a rocket immunoelectrophoresis technique, as described by C. B. Laurell in Analytical Biochemistry 15 (1966) at 45–52.

3 µl of a serum sample was pipetted into each of 10 identical wells 14 cut into a 1 mm thick agarose gel containing 1% of the T.B.G. antiserum with Barbitone/sodium Barbitone buffer, pH 8.6, 0.07 M. After electrophoresis for 6 hours at 20 volts the gel was press dried and stained with Coomassie Brilliant Blue R. The area of each rocket 15 was estimated (height × width at ½ height) and the coefficient of variation (standard deviation × 100/mean) was calculated.

As a further test of the effectiveness of the prepared antiserum in measuring T.B.G. under "routine" conditions ten separate estimations of the quantity of T.B.G. in a serum sample were made using different quantities of antiserum in the agarose gels. On consecutive days 1 mm thick agarose gels on 7.5×5 cm glass plates were formed containing from ½ to 3% of the T.B.G. antiserum and 5 wells were punched into each gel. A T.B.G. standard serum was diluted with the barbitone buffer to contain 50%, 25% and 12.5% of the original. 3 µl of undiluted standard and 3 µl of each dilution were pipetted into four of the five wells, the fifth was filled with 3 µl of an unknown serum sample. After electrophoresis, drying and staining, the areas of the precipitate arcs for the unknown sample were related to the calibration line drawn for the standards. The coefficient of variation in measuring the unknown sample was calculated. This coefficient of variation was 1.0% under optimal conditions and 2.9% under routine conditions.

We claim:
1. A process for the preparation of an antiserum, including steps of:
(i) reacting, by means of two dimensional electrophoresis a serum sample which includes a protein to which the required antiserum is to be specific, with a first antiserum sample which is known to include the required specific antiserum,
(ii) selecting, from the results of the aforesaid reaction, of a first antigen/antibody complex which corresponds to the protein to which the required antiserum is specific,

(iii) injecting an animal with said first complex, the antigen in said first complex being the only antigen so injected which was present in the serum which provided said serum sample, (iv) subsequent withdrawal of antiserum from the animal.

2. A process as claimed in claim 1 which includes the step of partially purifying said serum sample by physical means.

3. A process as claimed in claim 1 in which said first antiserum sample is obtained by injection into an animal of an electrophoretic fraction of a serum known to contain the protein to which the desired antiserum is to be specific.

4. A process as claimed in claim 1 in which selector of the, or each, antigen/antibody complex is effected by radioactive labelling, in the, or each, of said serum samples, of the protein to which the desired antiserum is specific.

5. An antiserum when produced by the method of claim 1.

6. A process as claimed in claim 1 which includes the further steps of:

(v) carrying out a further two-dimensional electrophoresis reaction between a serum sample which includes a protein to which the required antiserum is to be specific and a second antiserum sample provided by the serum withdrawn from the animal, (vi) determining if the antigen/antibody complexes resulting from said further reaction indicate that said withdrawn serum have the required specificity, (vii) if the required specificity is not present, selecting, from the results of said further reaction, second antigen/antibody complex which corresponds to the protein for which the required antiserum is to be specific, (viii) injecting a further animal with said second complex, the antigens in said second complex being the only antigens injected into said further animal from the serum which provided said serum sample.

7. A process as claimed in claim 1 in which the second dimension step of said electrophoresis reaction is continued for 24 hours.

* * * * *